United States Patent [19]

Ince

[11] 4,040,291
[45] Aug. 9, 1977

[54] HARDNESS TESTER

[75] Inventor: Bernard John Ince, Carlingford, Australia

[73] Assignee: Girlock Limited of Belmore, Australia

[21] Appl. No.: 656,944

[22] Filed: Feb. 10, 1976

[30] Foreign Application Priority Data

Feb. 21, 1975   Australia ............................... 0684/75

[51] Int. Cl.² ............................................... G01N 3/42
[52] U.S. Cl. ............................................ 73/81; 73/85
[58] Field of Search .................. 73/81, 83, 85, 37, 212

[56] References Cited

U.S. PATENT DOCUMENTS

| 1,192,670 | 7/1916 | Moore et al. | 73/81 |
| 2,679,163 | 5/1954 | Morris et al. | 73/212 |
| 3,116,478 | 12/1963 | Powell | 73/80 X |

Primary Examiner—Jerry W. Myracle

[57] ABSTRACT

A method of measuring surface hardness combining the techniques of Brinell Hardness testing and air-gauging by providing a hard penetrator member having in it a passage and apertures through which air under pressure is passed. The hardness of a work piece is measured by measuring the effect on air pressure caused by occlusion of the apertures as the penetrator is pressed into a specimen of which the hardness is to be measured.

8 Claims, 6 Drawing Figures

HARDNESS TESTER

The present invention relates to a method of measuring surface hardness and a tester therefor and more particularly to a method and tester for measuring the surface hardness of hard materials such as steel and cast iron or soft materials such as lead.

The hardness of materials such as steel and cast iron is normally measured by means of the Brinell method of hardness testing in which a hardened steel ball of a given diameter is impressed by means of a standard load into a surface of a specimen the hardness of which is to be measured and the diameter of the impression made is then measured by means of a microscope.

The normal procedure for carrying out a Brinell test for hardness of steels or irons consists of the following steps:

1. Smoothing the surface to be tested by filing, grinding or finishing.
2. Impressing a hardened steel ball of 5mm diameter at a force of 750 kilograms or a 10mm diameter ball at a force of 3,000 kilograms into the surface of the specimen.
3. Measuring by microscope the diameter of the impression made by the ball.
4. Using the measurement made for determining the Brinell hardness number from tables.

Considered in terms of a production line this is a fairly time consuming business and it is an object of the present invention to provide a method of hardness testing which is speedier and which can if desired be effected automatically in a production line.

The checking of measurements by means of a procedure known as air-gauging is well known in the engineering industry and involves essentially the measurement of the size of a gap or aperture by measuring the rate at which air will pass through it under predetermined conditions. The present invention uses a combination of Brinell hardness testing and air-gauging as a means of achieving the objects of the invention referred to above.

The invention consists in a method of measuring surface hardness by impressing into an object the hardness of which is to be measured, a hard penetrator member, such as a hard spherical or part spherical surface, there being therein a passage for the introduction of air under pressure and a hole or holes permitting the escape of air from said passage, the arrangement being such that the said hole or holes are partly occluded on impressing the member into the surface to be tested to an extent dependent on the hardness of the surface, introducing air under pressure, and determining the hardness of the surface by means of an air-gauging device arranged to measure the rate of flow of air through said partially occluded hole or holes.

The invention further consists in apparatus for carrying out the foregoing method.

In order that the invention may be better understood and put into practice a preferred form thereof is hereinafter described by way of example with reference to the accompanying drawings in which.

Figures 1, 2:
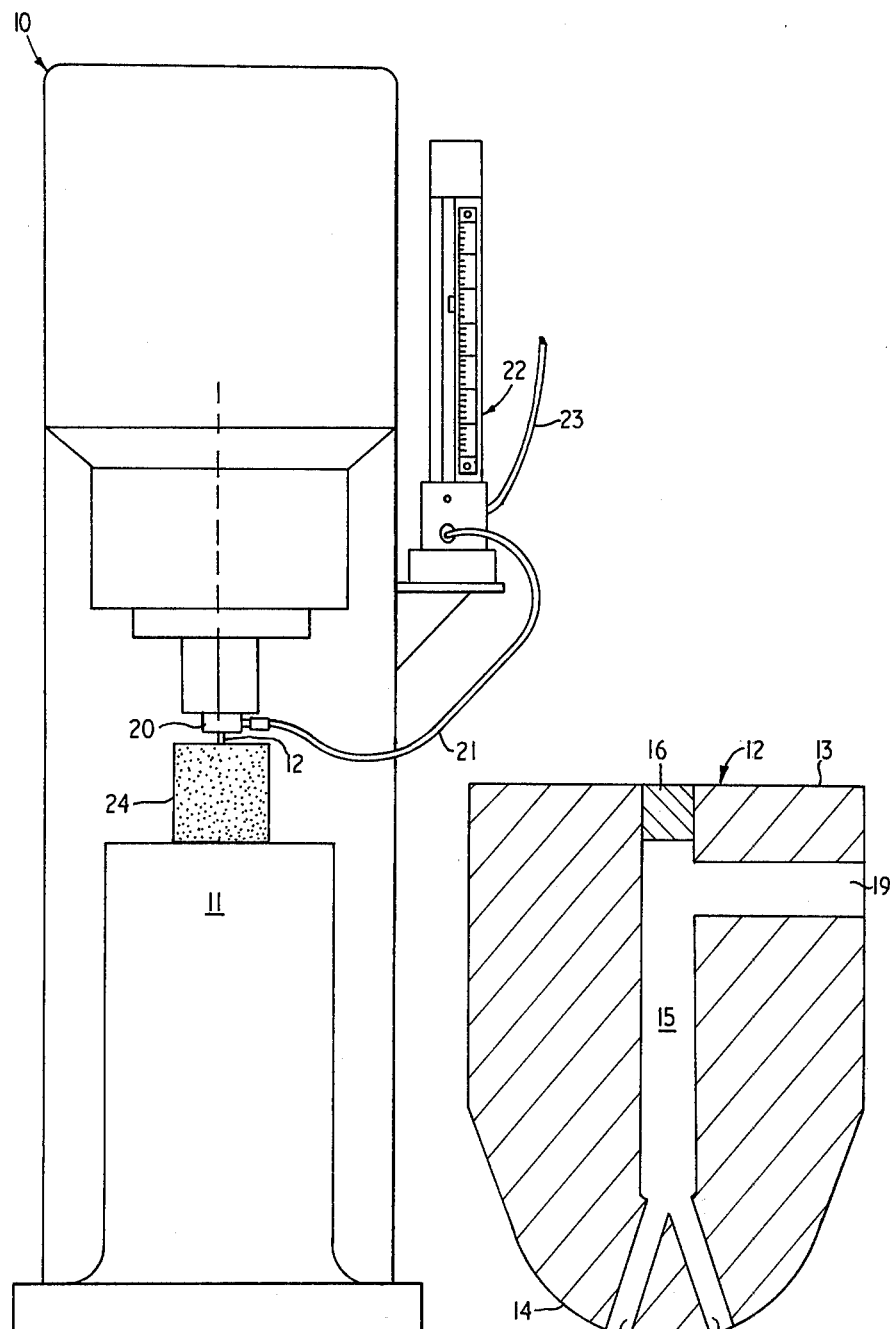
FIG. 1 is a diagrammatic elevation of a typical apparatus for carrying out the invention.
FIG. 2 is a sectional view to a greatly enlarged scale of a penetrator suitable for use in the apparatus of FIG. 1.

The apparatus shown in FIG. 1 consists of an hydraulic press 10 having a variable load facility and an anvil 11. Desirably the press is such that a particular load may be repeated within plus or minus 1%. As a standard hydraulic press may be used for the purposes of the invention it is not necessary to describe it in any detail. Mounted in the press is a penetrator 12 which is shown to a greatly enlarged scale in section in FIG. 2. The penetrator 12 consists of a body which may be made in hardened (850 min VPN) toolsteel or in tungsten carbide, preferably the latter.

In a particular apparatus used for testing the invention the penetrator shown in FIG. 2 was made from half inch diameter circular section material and was provided at one end with a flat face 13 square to the axis and at the other end with a part spherical portion 14 having a radius of 5mm. A central axial passage 15 of 0.06 inches in diameter was formed through the major part of the penetrator, the hole being blocked at its upper end by means of plug 16. At its lower end the passage 15 divides into two similar passages 17 and 18 each of 0.27 inches in diameter the axes of which are arranged at an angle of 37° 20'. The passages 17 and 18 open out into the part spherical surface 14 and the centres of the outlet holes are spaced apart a distance of 0.126 inches. A radially extending passage 19 connects with the passage 16. The overall length of the penetrator is approximately ¾ inch.

The penetrator 12 is mounted in a suitable holder 20 and the passage 19 is connected by means of a flexible tube 21 to a Sheffield single column air-gauge with a 5,000 : 1 magnification tube, the gauge being connected to a factory air supply through the flexible tube 23.

The part under test 24 was arranged on the anvil 11 with its upper test surface arranged so as to be within 5° of being square with the axis of the ram of the hydraulic press.

In order to gauge the hardness of the test material a predetermined pressure is applied to the penetrator to impress it into the surface of the part under test. As the part spherical portion 14 of the penetrator enters the test material the holes of the passages 17 and 18 will be wholly or partly occluded depending on the extent to which the penetrator enters the test material and thus on the hardness of the test material. It has been found that the degree of occlusion is a measure of the diameter of the impression formed in the test material and thus of its hardness. The degree of occlusion is measured by means of air-gauge 22 which in fact measures the resistance to the escape of air produced by the occlusion of the holes. It is found that in practice the time taken to obtain an indicative reading of hardness by this method is less than three seconds. It has also been found that if a dwell of 10 seconds is applied to the penetrator the Brinell Hardness number reading is reduced by up to 5 Brinell Hardness numbers but for all practical purposes the shorter period is quite adequate.

It is of course necessary to calibrate the apparatus and this is done by means of Avery Brinell test blocks or by direct Brinell microscope measurement. The latter method involves calculation of the Brinell formula, if a load other than a standard Brinell load is used.

Hardness measurements may be taken on "as cast" surfaces with an average skin finish and it is found that an accuracy of plus or minus 30 Brinell Hardness numbers can be obtained and this is quite adequate to detect, for example, a chilled casting since such a casting has a Brinell Hardness number of 400 plus whereas the normal range is of the order of 210–280 Brinell Hardness numbers. If however the surface of a casting is prepared by finishing, or machining, more accurate results can be obtained at little or no extra cost.

Figure 6:
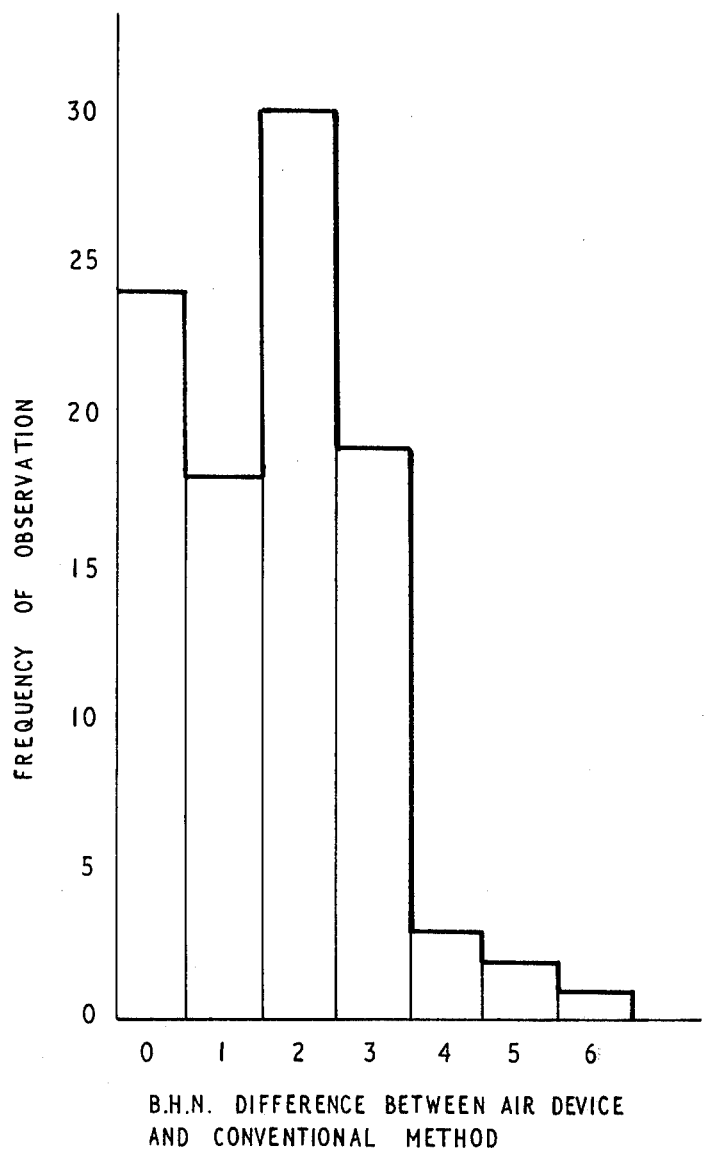

FIG. 6 illustrates results obtained from hourly sampling of continuous usage. Frequency of observation is plotted on the vertical axis and the difference in Brinell Hardness number obtained when using an apparatus according to the present invention and when obtained by the conventional method is shown on the horizontal axis. In evaluating these results it must be appreciated that it is not possible to test for Brinell Hardness twice in the same place and the comparisons given are for impressions taken approximately ⅜ of an inch apart in the same piece of iron, the impressions all being made in SG iron parts where a 25 Brinell Hardness number range over 4 inches is common. The statistical evaluation of the differences approximates to the Poisson distribution with expectation of 2, that is to say, with a maximum error six points different from the "absolute" reading given by a conventional Brinell Hardness test.

Figure 4:
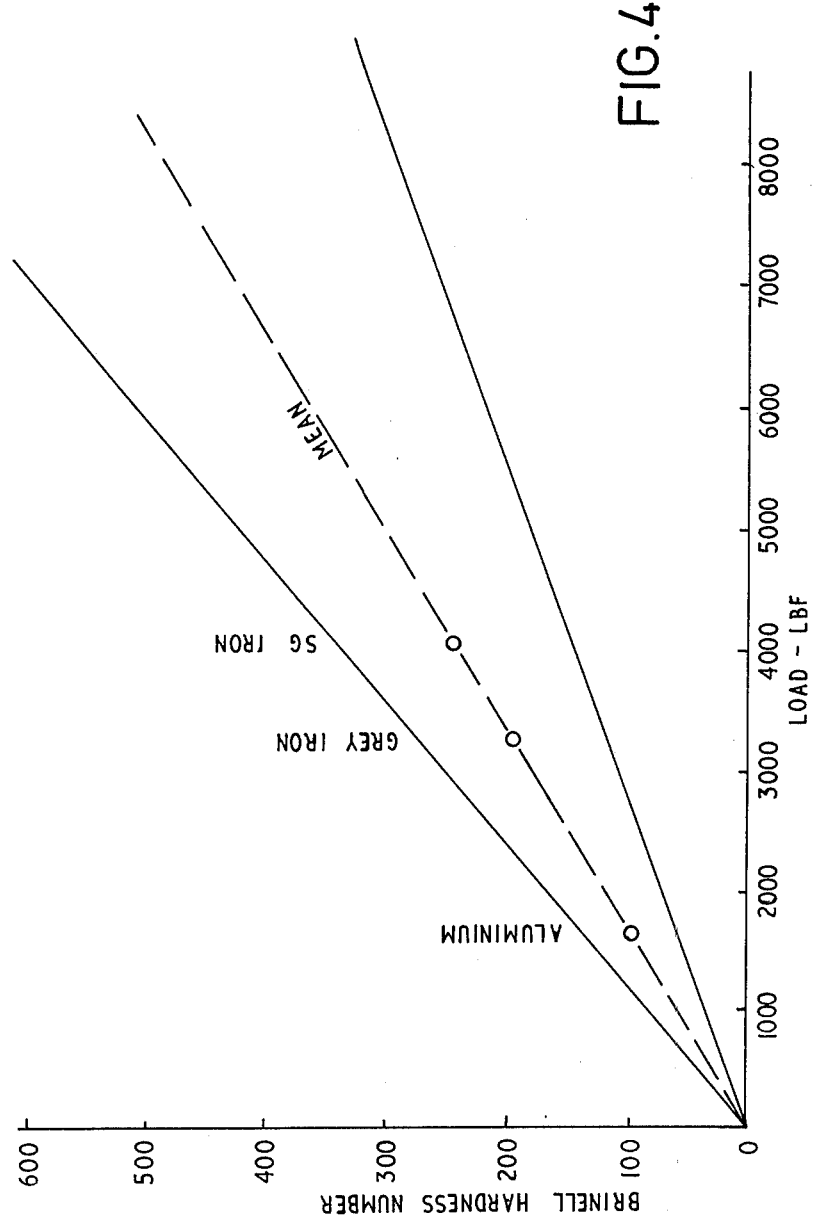
FIG. 4 is a graph illustrating the working range of an apparatus for carrying out the invention.

It became clear during testing that the invention could measure an infinite range of Brinell Hardness numbers purely by varying the load. This is illustrated in the graph shown in FIG. 4 in which Brinell Hardness numbers are plotted on the vertical axis against the load in pounds on the horizontal axis using the apparatus described above. The two full lines indicate the range of Brinell Hardness numbers that can be measured with the penetrator described above for a given load. It will be appreciated that if the hardness of the material is too low the holes will be completely occluded whereas if it is too high the holes will not be occluded at all. Points are shown on the mean line indicative of the approximate hardness of aluminium, grey iron and SG iron. By varying the size and pitch of the holes (17 and 18 FIG. 2) other combinations of load and Brinell can be achieved.

Figure 5:
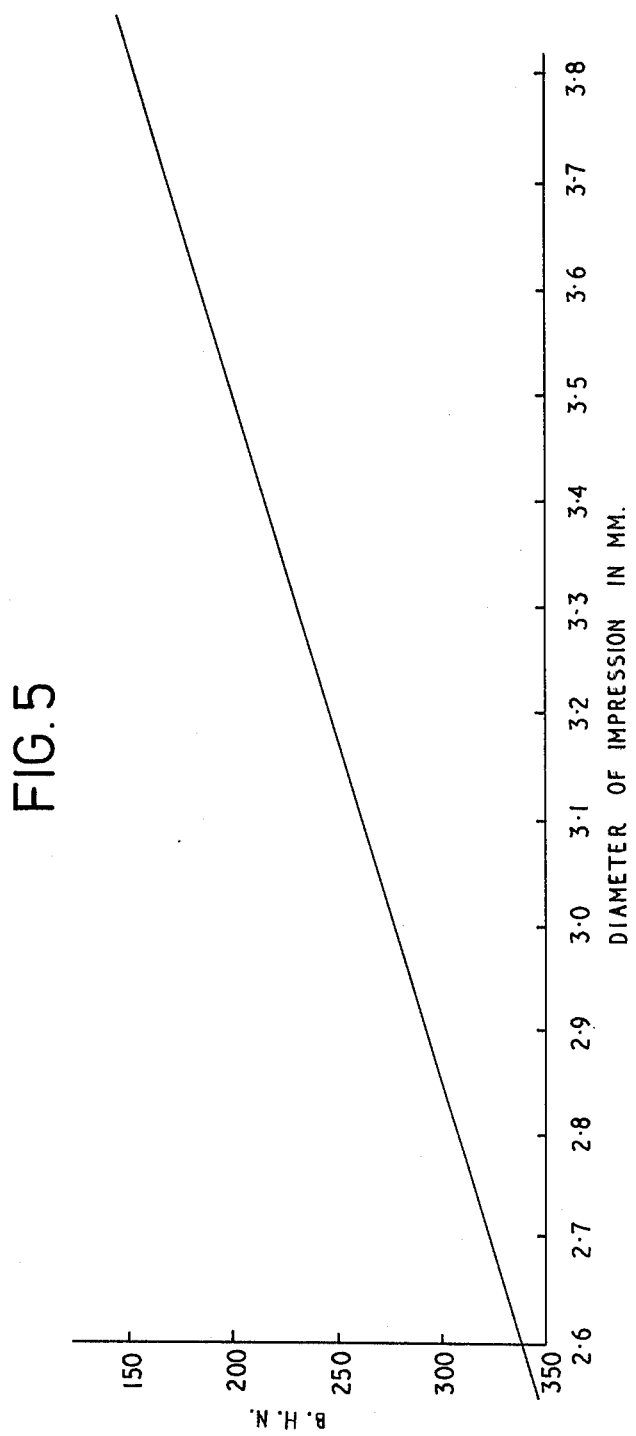
FIG. 5 is a graph of the relationship between Brinell Hardness number and impression diameter for the apparatus and FIG. 6 is a comparative illustration of the results achieved by use of the invention and with a conventional Brinell Hardness tester.

FIG. 5 shows the relationship between Brinell Hardness number (vertical axis) and impression diameter in millimeters using a loading of 4,000 pounds with the penetrator described above.

Figure 3:
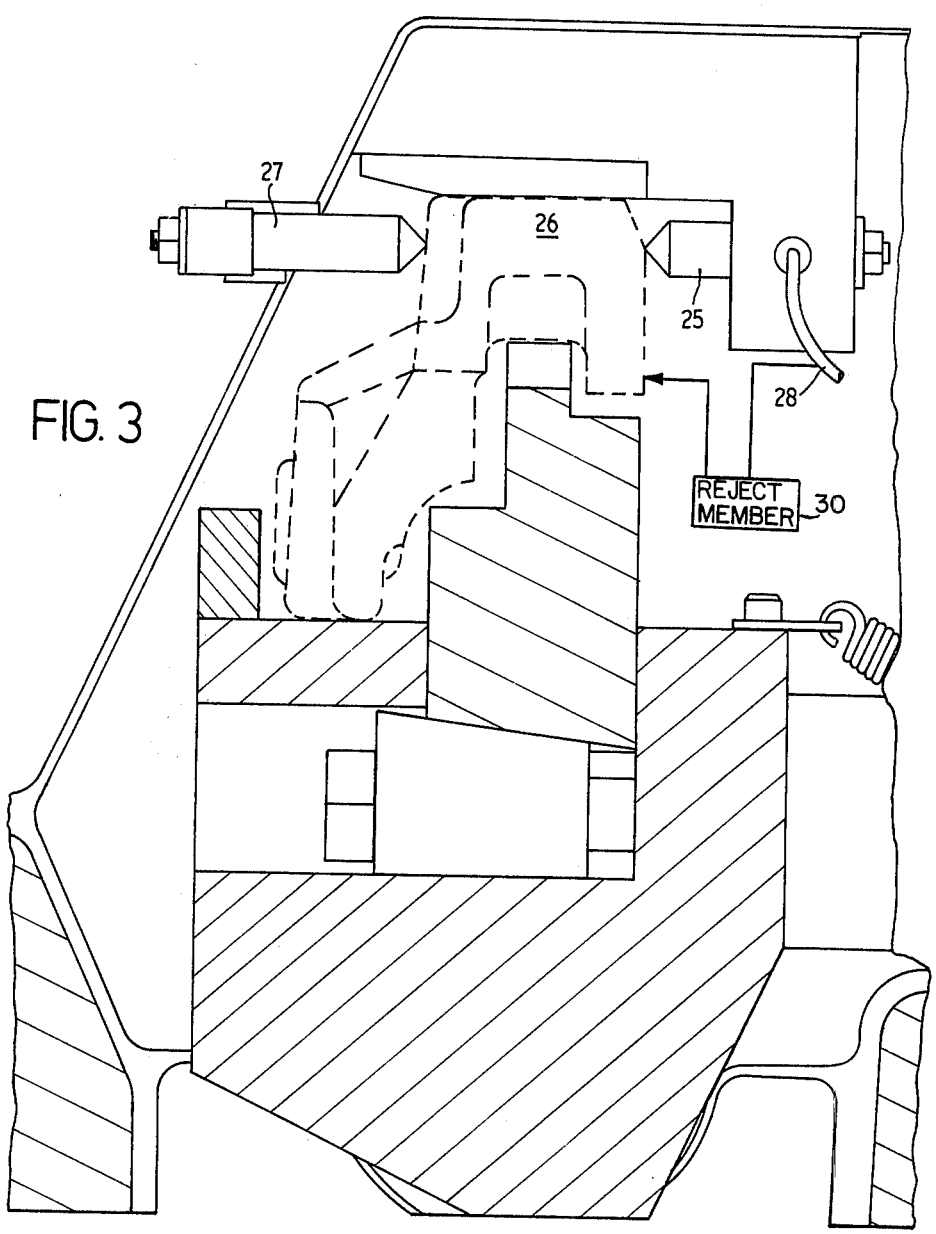
FIG. 3 is a sectional view illustrating the application of the invention as a hardness monitor on a machine tool fixture.

The invention may be readily adapted for use as an automatic hardness testing device applied to machining processes and is of particular advantage in highly mechanised processes such as in transfer machines and may be used to avoid expensive damage to cutting tools caused by their being offered up to a casting, the surface of which is so hard as to damage the tools. In such an application illustrated in FIG. 3 the penetrator 25 is used as a jig locating point or clamp. The component 26 to be tested is held between the penetrator 25 and a clamp 27. By ensuring that a constant load is applied during the clamping operation a signal indicative of the hardness of the work piece can be obtained, the air-gauging device to which the penetrator 25 is connected by means of a flexible pipe 28 being set up to signal the machine to proceed if the casting is of satisfactory hardness or to stop automatically if the hardness is unsatisfactory. A conventional reject member 30 also could be utilized to automatically reject unsatisfactory castings in response to the pressure in pipe 28.

While the penetrator illustrated in FIG. 2 is the most satisfactory device to date, it is proposed to construct a penetrator of substantially frusto-conical form with sides at a fairly acute angle and the holes opening into the sides, the object being to provide a greater range of movement of the penetrator between the point at which the holes are not occluded and that at which they are completely occluded with a view to providing greater accuracy.

While it has been found that the provision of two holes in the penetrator is extremely satisfactory for smooth surfaces there are reasons to believe that its performance could be improved on rough surfaces by the provision of for example four holes with a view to evening out the effect of surface roughness on the extent to which the holes are occluded. The holes are formed in the penetrator either by drilling before hardening or by means of spark erosion and no particular difficulty is expected to arise in the formation of four holes.

In the application of the invention to automatic operation of a machine tool it is desirable to provide suitable valving whereby the penetrator is occasionally purged with full air line pressure in order to blow out any accumulated dust or graphite. With holes of the size in the penetrator described above no clogging has been encountered when used on dry machined surfaces but in earlier trials with a penetrator having a 5 millimeter diameter part-spherical surface and 0.013 inch diameter holes clogging tended to occur after 5,000 applications when used on oily as cast surfaces. This did not impair accuracy but it did slow the air-gauge response.

We claim:

1. A method of measuring surface hardness by impressing into an object the hardness of which is to be measured, a hard penetrator member, there being therein a passage for the introduction of air under pressure and a hole or holes permitting the escape of air from the said passage, the arrangement being such that the said hole or holes are partly occluded on impressing the member into the surface to be tested to an extent dependent on the hardness of the surface, introducing air under pressure, and determining the hardness of the surface by means of an air-gauging device arranged to measure the rate of flow of air through said partially occluded hole or holes.

2. Apparatus for measuring surface hardness of an object consisting of a hard penetrator member, an air passage in said member opening in a hole or holes in a surface of the member, means for impressing said surface of said member into an object the hardness of which is to be measured in such a manner that the said hole or holes are partially occluded by penetration of the member into the object, means for introducing air under pressure into said passage and air-gauging means for measuring the rate of flow of air through said partially occluded hole or holes.

3. Apparatus as claimed in claim 2 wherein said surface is a part-spherical surface and said passage opens into two or more holes arranged symmetrically about the axis of said surface.

4. Apparatus as claimed in claim 2 wherein the penetrator member constitutes a jig locating point or clamp in a machine tool and means are provided to clamp a series of objects in turn against said member with a similar pressure in each case and wherein means are provided to cause said machine tool to reject any object the hardness of which does not fall within a predetermined range of hardness.

5. A penetrator member for measuring surface hardness of an object comprising:

marker means having a hardened end for making an impression in said object when said end is pressed there against;

hole means defining an aperture in said end of said marker means;

passage means for placing said hole means in communication with a pressure source.

6. A penetration member as claimed in claim 5 wherein said end is part-spherical.

7. The penetrator of claim 5 wherein said marker means is comprised of end material selected from the group comprising steel, hardened steel, or tungsten carbide.

8. The penetrator of claim 5 wherein said hole means is comprised of plural passages symmetrically oriented on said end of said marker means.

* * * * *